United States Patent [19]

Crowninshield et al.

[11] Patent Number: 4,795,472
[45] Date of Patent: Jan. 3, 1989

[54] PROSTHESIS WITH ENHANCED SURFACE FINISH

[75] Inventors: Roy D. Crowninshield; Arden R. Zolman, both of Warsaw, Ind.

[73] Assignee: Zimmer, Inc., Warsaw, Ind.

[21] Appl. No.: 7,538

[22] Filed: Jan. 28, 1987

[51] Int. Cl.⁴ .................................................. A61F 2/32
[52] U.S. Cl. .......................................... 623/23; 623/18
[58] Field of Search ................. 623/16, 17, 18, 19, 623/20, 21, 22, 23

[56] References Cited

U.S. PATENT DOCUMENTS

| | | | |
|---|---|---|---|
| 2,718,228 | 9/1955 | Steenbrugghe | 128/92 |
| 3,894,297 | 7/1975 | Mittelmeier et al. | 3/1 |
| 4,081,866 | 4/1978 | Upshaw et al. | 623/20 |
| 4,199,824 | 4/1980 | Niederer | 3/1.913 |
| 4,261,063 | 4/1981 | Blanquaert | 3/1.91 |
| 4,280,233 | 7/1981 | Raab | 3/1.91 |
| 4,281,420 | 8/1981 | Raab | 3/1.912 |
| 4,283,799 | 8/1981 | Pratt, Jr. et al. | 3/1.913 |
| 4,336,618 | 6/1982 | Raab | 3/1.913 |
| 4,365,359 | 12/1982 | Raab | 3/1.912 |
| 4,430,761 | 2/1984 | Niederer et al. | 3/1.91 |
| 4,491,987 | 1/1985 | Park | 3/1.91 |
| 4,514,865 | 5/1985 | Harris | 3/1.913 |
| 4,530,116 | 7/1985 | Frey | 623/23 |
| 4,535,487 | 8/1985 | Esper et al. | 623/22 |
| 4,549,319 | 10/1985 | Meyer | 623/22 |
| 4,566,138 | 1/1986 | Lewis | 623/22 |
| 4,608,052 | 8/1986 | Van Kampen et al. | 623/22 |
| 4,608,053 | 8/1986 | Keller | 623/23 |

FOREIGN PATENT DOCUMENTS

| | | |
|---|---|---|
| 0025814 | 4/1981 | European Pat. Off. |
| 0131178 | 1/1985 | European Pat. Off. |
| 0158534 | 10/1985 | European Pat. Off. |
| 0169976 | 2/1986 | European Pat. Off. |
| 2575384 | 7/1986 | France ............ 623/23 |
| 560042 | 3/1975 | Switzerland |

OTHER PUBLICATIONS

"Poly (Methyl Methacrylate) Precoating of Orthopaedic Implants"-Zimmer, Inc.-Literature No. 85-000-00-00-0269 Rev. 2-1984.
"Poly Methyl Methacrylate (PMMA) Precoating of Surgical Implants"-Zimmer, Inc., 1985.
"Harris Precoat Hip Prosthesis-The Total System'-'-Zimmer, Inc.-Literature No. 97-9026-101-00-1986.
"Precise Fixation—Proximally and Distally-Unique Distal Sleeve"-Dow Corning Wright-No date available.
"The Howmedica Precision Hip System"-Howmedica, Div. of Pfizer Hospital Products Group, Inc., 1986.
"Integrated Systems of Implants and Instrumentation'-'-Ostoenics Corp.-Literature No. PF-4-1984.
"The Bio-Fit Stem"-Richards Medical Company-1985.
"Cementless Ceramic Total Hip Replacement"-Richards Medical Company-1983.
"Aesculap-P. M. Total Hip System"-Aesculap-Werke AG-Aesculap Instruments Corp.-No data available.
"Anatomical Hip Endoprothesis System Lubeck"-S & G Implants-No date available.
"CLS Cementless Hip Stem"-Protek-No date available.
"The Freeman Total Hip System"-Corin Medical Limited-JBJS, vol. 68-A, No. 1, Jan. 1986.
"A New Approach to Cementless Implant Fixation'-'-Link America, Inc.-No date available.
"Macrofit Hip-Femoral Prosthesis (Collared and Collarless)"-Zimmer, Inc.-Literature No. 86-037-65-40-0528, 1986.

Primary Examiner—Richard J. Apley
Assistant Examiner—David J. Isabella
Attorney, Agent, or Firm—Margaret L. Geringer

[57] ABSTRACT

An orthopaedic prosthesis for implantation with a bone cement composition, the prosthesis including a polymer coating and a textured surface underneath at least a portion of the polymer coating. The textured surface, which is visible to the eye without magnification, beneath the polymer coating enhances or increases the surface shear and tensile strength of the prosthesis.

5 Claims, 1 Drawing Sheet

U.S. Patent    Jan. 3, 1989    4,795,472
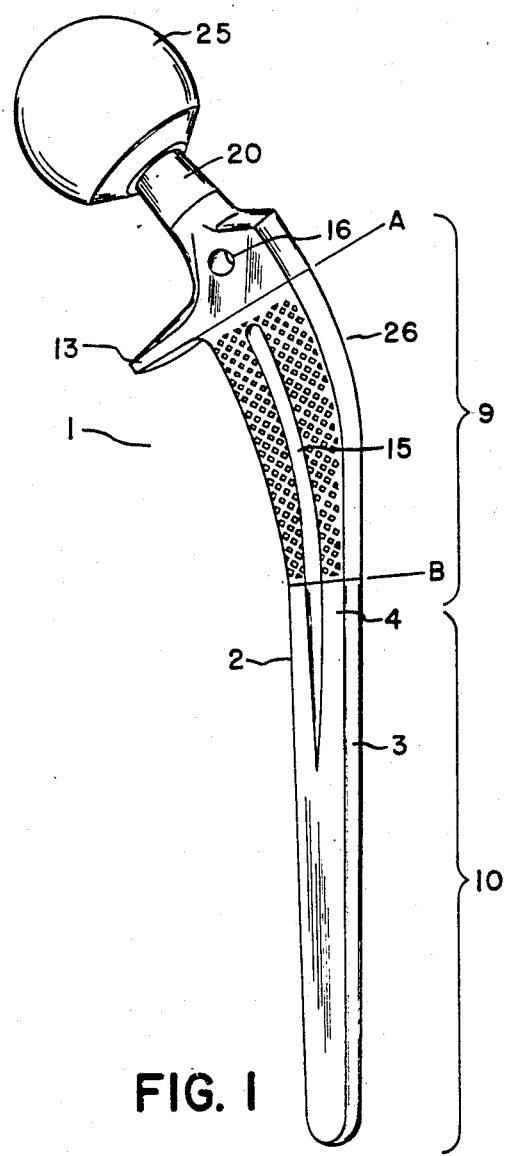
FIG. 1
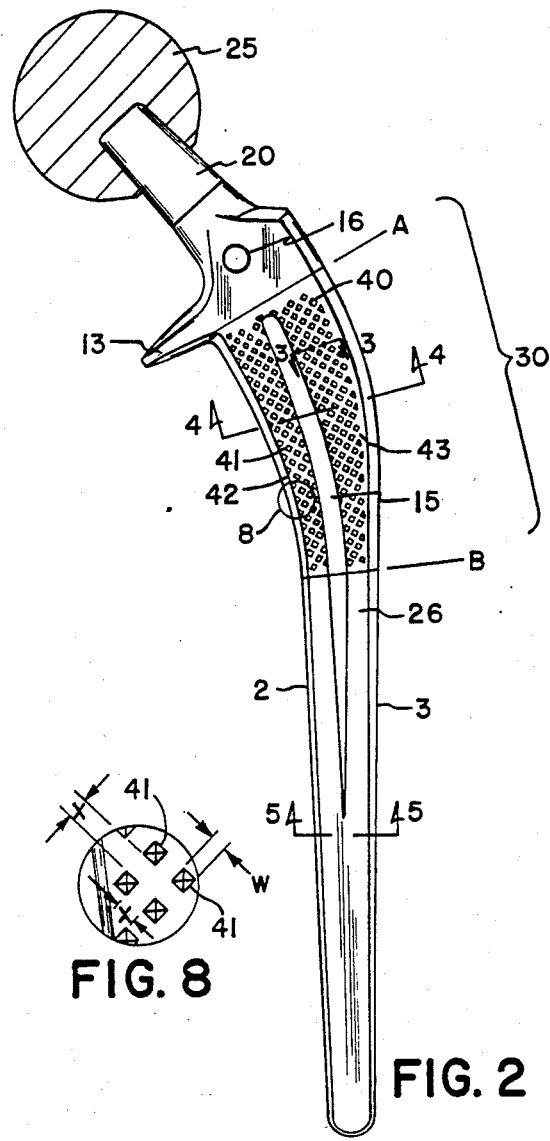
FIG. 8
FIG. 2
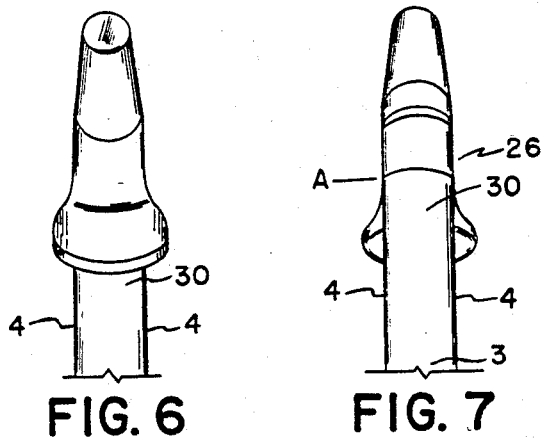
FIG. 6    FIG. 7    FIG. 4    FIG. 5
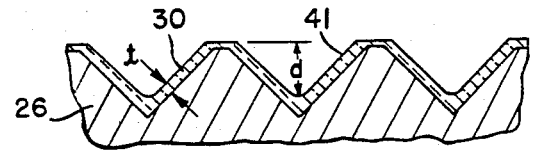
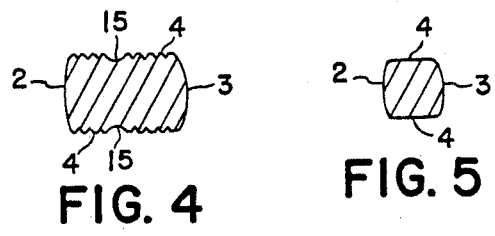
FIG. 3

PROSTHESIS WITH ENHANCED SURFACE FINISH

BACKGROUND OF THE INVENTION

The present invention relates to an orthopaedic prosthesis, and more particularly to a prosthesis with an enhanced surface finish for more secure fixation.

The precoating of prosthetic implants with a polymer coating is disclosed in U.S. Pat. No. 4,491,987 to Park and in U.S. Pat. Nos. 4,336,618; 4,365,359; 4,281,420; and 4,280,233 to Raab. In addition, U.S. Pat. No. 4,283,799 to Pratt, Jr., et al. discloses a method of implanting a prosthesis which includes precoating the skeletal cavity and implant stem, allowing both to cure, then applying further cement to the cavity before insertion of the stem. U.S. Pat. No. 4,514,865 to Harris also discloses an embodiment (see FIGS. 6 and 7 of Harris) in which an implant stem is precoated with a film of cement.

Numerous types of texturing are known for use on prosthetic implants. The following are representative of such texturing:

U.S. Pat. No. 4,608,053—Keller
U.S. Pat. No. 4,608,052—Van Kampen, et al.
U.S. Pat. No. 4,549,319—Meyer
U.S. Pat. No. 4,535,487—Esper, et al.
U.S. Pat. No. 4,530,116—Frey
U.S. Pat. No. 4,430,761—Nierderer, et al.
U.S. Pat. No. 4,261,063—Blanquaert
U.S. Pat. No. 4,199,824—Nierderer
U.S. Pat. No. 3,894,297—Mittelmeier, et al.
U.S. Pat. No. 2,718,228—Van Steenbrugghe
European Application No. EP 0 169 976 A1—Griss
European Application No. EP 0 158 534 A2—Freeman
European Application No. EP 0 131 178 A2—Link
European Application EP 0 025 814 A1—Seidel, et al.
Swiss Patent No. 560,042—Locke Heretofor, prosthetic implants including a precoat of a polymer coating have been incorporated on an untextured surface. While U.S. Pat. No. 4,491,987 describes a pretreatment of the implant surface which is to be coated, this pretreatment of sulfuric acid, sandblasting, or the like is to prepare a fresh "roughened" surface to improve the bonding between the prosthesis and the polymer coating. However, it is noted that this "roughening" of the surface generally does not provide any substantial roughening which is visible to the eye without magnification. Accordingly, the surface is still generally smooth to the eye and does not provide any surface texturing to the implant. Precoating of an implant with a polymer coating increases the shear (sliding) strength and increases the tension (pulling) strength of an implant over an uncoated implant. In addition, precoating enhances the bond of the precoated implant to bone cement upon implantation with cement, improving the bonding over an uncoated implant.

Texturing for the sake of this specification is defined to be a rough or unsmooth surface which is visible to the eye without magnification, often referred to in the art as "macrotexturing." Such texturing of implant surfaces has been widely used as indicated by the above-listed patents regarding texturing. Texturing of an implant surface also tends to increase the shear strength over an untextured implant surface; however, texturing provides only a small increase in tension strength.

U.S. Pat. No. 4,566,138 to Lewis, et al., is also cited for general information. It includes an implant with a plurality of acrylic spacers adhered to a porous outer surface. The acrylic spacers provide a uniform space between the bone and prosthetic device to uniformly control the thickness of cement. The acrylic spacers are raised stubs covering only a small portion of the porous surface and such spacers are not a coating.

OBJECTS OF THE INVENTION

A principle object of the invention is to provide an orthopaedic prosthesis which includes an enhanced surface finish to strengthen the bond between the prosthesis and the bone cement composition which is used during implantation of the prosthesis.

Another object of the invention is to provide an orthopaedic implant which provides both increased pull-out (tensile) strength and increased push-out (shear) strength.

SUMMARY OF THE INVENTION

The present invention provides an orthopaedic prosthesis which includes a polymer coating and a textured surface underneath at least a portion of the polymer coating. The textured surface preferably includes a plurality of indentations in the base material that are readily visible without magnification. The indentations are preferably uniformly spaced and sized in a predetermined pattern with the textured surface being substantially confined to within the area of the polymer coating. This orthopaedic implant thus has an enhanced surface finish which strengthens the bond between the implant and bone cement which is used during implantation of the prosthesis.

BRIEF DESCRIPTION OF THE DRAWINGS

These features and objects of the invention, as well as others, will become apparent to those skilled in the art by referring to the accompanying drawings:

FIG. 1 is a perspective view of a hip stem implant according to the present invention;

FIG. 2 is a side elevational view of the hip stem of FIG. 1 shown in partial cross-section;

FIG. 3 is an enlarged partial cross-sectional view taken along lines 3—3 of FIG. 2;

FIG. 4 is a cross-sectional view taken along lines 4—4 of FIG. 2;

FIG. 5 is a cross-sectional view taken along lines 5—5 of FIG. 2;

FIG. 6 is a partial front elevational view of the hip stem;

FIG. 7 is a partial rear elevational view of the hip stem;

FIG. 8 is an enlarged partial side elevational view of the textured indentations taken at circle 8 of FIG. 2.

DETAILED DESCRIPTION OF THE INVENTION

FIGS. 1–8 illustrate a particularly advantageous embodiment of an orthopaedic implant according to the present invention. The invention will be described with reference to a hip prosthesis implant; however, it is understood that the principles of the invention are applicable to any suitable prosthetic implant. In addition, the implant of the present invention is primarily intended for implantation within a warm-blooded mammal with a bone cement composition at the time of surgery, although the features of the invention are not limited solely thereto.

The prosthetic hip implant 1 of FIG. 1 includes a head 25 and a stem 26. The head 25 may be integrally formed with the stem 26 or it may be a separate component from the stem 26, such as is shown in FIGS. 1 and 2. The stem 26 includes a proximal end 9 and a distal end 10. Generally, the proximal end 9 is considered to be approximately the top half portion of the stem 26, and the distal end 10 is considered to be approximately the bottom half portion of the stem 26. The stem 26 includes a pair of approximately opposite sidewalls 4 separated by a medial side 2 and a lateral side 3.

The prosthetic hip implant 1 is comprised of a suitable base material structurally defined as to shape and strength to assimilate a portion of hard mammal tissue. In FIGS. 1-8, the hip prosthesis 1 is formed to replace a portion of the proximal human femur. The base material of the hip prosthesis 1 may be formed of any suitably strong material, such as a cobalt-chromium alloy or other biologically compatible material.

The stem 26 includes a polymer coating 30 about an area of the hip prosthesis for contact with bone cement during implantation to achieve a chemical bond therebetween. The polymer coating is substantially completely polymerized as a coating on the hip prosthesis 1 prior to the implantation. During implantation of the prosthesis 1 with fresh bone cement at the time of surgery, the polymer coating 30 will become securely bonded to the fresh bone cement as the fresh bone cement polymerizes.

The hip prosthesis 1 further includes a textured surface 40 over a portion of the base material underneath at least a portion of the polymer coating 30. The textured surface 30 is preferably confined to within the area of the polymer coating 30. The coating 30 is shown in FIGS. 1 and 2 to extend from line A to line B as a continuous circumferential coating, thus completely covering the exposed surface area between lines A and B and surrounding the four sides 2, 3, and 4 of the stem 26.

The textured surface may include a wide variety of "unsmooth" surface features, such texturing being visible to the eye without magnification. The textured surface 40 preferably includes a plurality of indentations 41 in the base material that are readily visible to the eye. The indentations 41 are uniformly spaced and sized in a predetermined pattern. The indentations 41 or textured surface 40 substantially increase the exposed surface area of the base material which is to be precoated with the polymer coating. This will increase the surface area of polymer coating which will be in contact with the fresh bone cement in the coated area 30 of the hip prosthesis 1. The indentations 41 of the embodiment shown are each shaped substantially in the form of an inverted pyramid as shown in FIG. 8.

The indentations 41 preferably have a depth "d" (see FIG. 3) of approximately 0.254 millimeters (0.010 inches). However, the indentations may have a minimum depth of about 0.127 millimeters (0.005 inches) and may range to a maximum of about 0.762 millimeters (0.30 inches). The indentations 41 preferably have a width opening "w" (see FIG. 8) of about 0.762 millimeters (0.030 inches). However, the indentations may have a minimum width opening of about 0.508 millimeters (0.020 inches) and may range to a maximum opening of about 2.032 millimeters (0.080 inches). The indentations may be suitably arranged uniformly in diagonal rows (see FIGS. 1 and 2) with the rows preferably being spaced apart by a length "X" (see FIG. 8) of about 0.508 millimeters (0.020 inches). However, the diagonal rows of indentations may be a minimum length apart of about 0.254 millimeters (0.010 inches) and may range to a maximum of about 1.524 millimeters (0.060 inches).

As shown in FIGS. 1 and 2, the polymer coating 30 and the textured surface 40 of the plurality of indentations 41 preferably are substantially in the proximal end 9 of the stem 26 and do not extend into the distal end 10 of the stem 26. The polymer coating 30 uniformly and continuously covers the surface of the pair of sidewalls 4, the medial side 2 and the lateral side 3 providing a continuous circumferential coating about the proximal end 9. The textured surface, however, is preferably not included on the medial side 2 or the lateral side 3 but is included on at least one and preferably both of the pair of sidewalls 4. Thus, it can be seen that the textured surface 40 is preferably confined to within the area of the polymer coating 30, and while the textured surface 40 is underneath at least a portion of the polymer coating 30, it is not necessarily included under the whole precoated area.

The sidewalls 4 further include an elongated groove 15 extending along the length of the proximal end 9. The groove 15 is untextured and separates the textured surface 40 on the sidewalls 4 into a medial textured surface 42 and a lateral textured surface 43. The groove 15 extends through at least a majority of the precoated proximal end 9 of the stem 26 and may further extend into the uncoated and untextured distal end 10.

As shown in FIGS. 1, 2, 6, and 7, the hip implant may include a collar 13 projecting from the stem 26 just below the transition to the neck 20 of the stem 26. In addition, a thru hole 16 may be provided in the uppermost portion of the proximal end 9 (above the precoat boundary line A) to engage a suitable instrument in order to facilitate stem extraction, as is known in the art.

The polymer coating 30 is uniform in thickness about the prosthesis 1 and is preferably about 60 microns (0.00236 inches) thick as shown by "t" in FIG. 3. However, the coating 30 may have a minimum thickness of about 20 microns (0.00079 inches) and may range to a maximum of about 200 microns (0.00787 inches). The polymer coating 30 may be applied by any suitable means including the coating methods disclosed in Park (U.S. Pat. No. 4,491,987) and Raab (U.S. Pat. Nos. 4,336,168; 4,365,359; 4,281,420; and 4,280,233) which, as such, are each incorporated herein by reference. Accordingly, the polymer coating 30 may be a polymethyl methacrylate composition or other suitable polymer composition.

The prosthesis of the present invention may be manufactured by forming the orthopaedic implant into a predetermined shape from a suitable base material, such as a cobalt-chromium alloy or other suitable biologically acceptable material. The implant may be formed by forging or other appropriate manufacturing processes. The desired shape may be fine-tuned by polishing or other standard processes, as needed. The textured surface 40 which includes readily visible roughening or indentations to the surface is then applied to the proximal end 9 of the sidewalls 4. This can be done by pressing the texture on with a die insert on a hydraulic press or utilizing other suitable manufacturing means. The implant is then pretreated to provide a fresh roughened surface in preparation for receiving the polymer coating. As previously mentioned, the roughened surface that results from the pretreatment is not a readily perceptible roughness but is more of a finer roughening of the surface (a micro or fine roughening) which is prepared by sandblasting, acid etching, or the like. If the typical "roughness" of the pretreated implant surface was measured upon magnification of the surface, the depth of irregularities in the surface would be minimal, about 15 microns (0.00064 inches) versus the approximate *minimum* depth of the macro or visible indentations 41 in the textured surface 40, which was previously noted as about 0.127 millimeters (0.005 inches). The polymer coating is then uniformly applied to the proximal end from line A to line B on the sidewalls 4, the medial side 2 and the lateral side 3 to provide a continuous circumferential coating about the proximal end 9 and substantially completely covering the textured surface 40 on the sidewalls 4 with the coating 30. The polymer coating then substantially completely polymerizes on the implant 1.

The resulting implant which includes the textured surface 40 underneath the polymer precoat 30 provides an increased surface area of contact for intimate contact with the fresh bone cement at the time of implantation, thus enhancing the bonding of the precoated implant to the new bone element. The relative magnitude of the improved bonding strength is represented in the following Table 1. Table 1 is representative of tests conducted with cobalt chromium alloy test specimens which have been inserted into fresh cement which is then allowed to polymerize to bond with the test specimens.

| Surface Finish of Test Specimens | Pull-out (Tensile) Strength - PSI | Push-out (Shear) Strength - PSI |
|---|---|---|
| Standard implant finish | 781 | 259 |
| Surface Texturing only | 909 | 1303 |
| Polymer coating only | 1437 | 1328 |
| Polymer coating, plus surface texturing | 1622 | 2029 |

It is readily seen that the surface which incorporates the polymer coating 30 plus the macrotexturing 40 significantly enhances the bonding strength of the implant in both tensile and shear but especially in shear strength. Thus, the implant of the present invention has an enhanced surface finish. While this invention has been described and exemplified, in terms of a particularly advantageous embodiment those skilled in the art can appreciate that modifications can be made without departing from the spirit and scope of this invention.

We claim:

1. An orthopaedic prosthesis comprising a base material, the prosthesis having a polymer coating about an area of the prosthesis, the coating being substantially completely polymerized, and the prosthesis further including a textured surface over a portion of the base material underneath at least a portion of the polymer coating, wherein the textured surface is a macrotextured surface which includes a plurality of indentations in the base material that are readily visible without magnification and wherein the polymer coating is uniform in thickness about the prosthesis, thus providing an indented, nonsmooth polymer surface wherein the polymer coating does not completely fill up the indentations, but wherein the polymer surface has indentations therein.

2. The prosthesis of claim 1 wherein the base material includes a stem having a proximal end and a distal end and a pair of sidewalls interconnected by a medial side and a lateral side, and wherein the textured surface is confined substantially to within the area of the polymer coating.

3. The prosthesis of claim 2 wherein the polymer coating and plurality of indentations are substantially in the proximal end of the stem and do not extend into the distal end of the stem.

4. The prosthesis of claim 3 wherein the polymer coating in the proximal end uniformly and continuously covers the surface of the pair of sidewalls and the medial and lateral sides while the textured surface is not included on the medial and lateral sides but is included on at least one of the pair of sidewalls.

5. A method of manufacturing an orthopaedic implant including the following steps:
   a. forming the orthopaedic implant into a predetermined shape from a suitable base material;
   b. applying a macrotextured surface on a portion of the implant surface in which the macrotextured surface includes a plurality of indentations in the base material which are readily visible without magnification;
   c. pretreating the implant surface to provide a fresh, roughened surface in preparation for receiving a polymer coating;
   d. applying a polymer coating to the prepared pretreated surface such that the textured surface is underneath at least a portion of the polymer coating and substantially confining the macrotextured surface to within the area of the polymer coating; and
   e. permitting the polymer coating to substantially completely polymerize on the implant.

* * * * *